(12) United States Patent
Kim (10) Patent No.: US 11,071,540 B2
(45) Date of Patent: Jul. 27, 2021

(54) LIFTING MEMBER

(71) Applicant: DONGBANG MEDICAL CO., LTD., Chungcheongnam-do (KR)

(72) Inventor: Keun Shik Kim, Chungcheongnam-do (KR)

(73) Assignee: DONGBANG MEDICAL CO., LTD., Chungcheongnam-do (KR)

( * ) Notice: Subject to any disclaimer, the term of this patent is extended or adjusted under 35 U.S.C. 154(b) by 219 days.

(21) Appl. No.: 16/313,279

(22) PCT Filed: Jun. 30, 2017

(86) PCT No.: PCT/KR2017/006930
§ 371 (c)(1),
(2) Date: Dec. 26, 2018

(87) PCT Pub. No.: WO2018/004286
PCT Pub. Date: Jan. 4, 2018

(65) Prior Publication Data
US 2019/0159773 A1     May 30, 2019

(30) Foreign Application Priority Data

Jun. 30, 2016 (KR) .................. 10-2016-0082865
Jun. 5, 2017 (KR) .................. 10-2017-0069637

(51) Int. Cl.
*A61B 17/06*     (2006.01)
*A61M 37/00*     (2006.01)
(Continued)

(52) U.S. Cl.
CPC ............. *A61B 17/06* (2013.01); *A61B 17/00* (2013.01); *A61B 17/04* (2013.01);
(Continued)

(58) Field of Classification Search
CPC ......... A61B 17/34; A61B 17/00; A61B 17/04; A61B 17/06; A61B 17/0482; A61B 39/04;
(Continued)

(56) References Cited

U.S. PATENT DOCUMENTS

2015/0272556 A1*   10/2015   Lee .................. A61B 10/04
                                                  600/566

FOREIGN PATENT DOCUMENTS

JP     2013103077 A    5/2013
KR     101397519 B1    1/2014
(Continued)

OTHER PUBLICATIONS

Pothier, Andrew, "Office Action Regarding Canadian Patent Application No. 3029304", dated Nov. 26, 2019, p. 6, Published in: CA.
(Continued)

*Primary Examiner* — George J Ulsh
(74) *Attorney, Agent, or Firm* — Neugeboren O'Dowd PC (57) ABSTRACT

The present invention provides a lifting member which easily inserts a medical thread into a muscle and induces the generation of an autogenous material. For example, the lifting member according to the present invention comprises: a needle having a through hole which is formed therein along the longitudinal direction; and a medical thread coupled to the outer circumference of the needle, wherein the medical thread may be finished to enwrap the end of the needle.

16 Claims, 7 Drawing Sheets

(51) Int. Cl.
  *A61B 17/00* (2006.01)
  *A61F 2/00* (2006.01)
  *A61M 5/32* (2006.01)
  *A61B 17/34* (2006.01)
  *A61B 17/04* (2006.01)
  *A61M 5/158* (2006.01)

(52) U.S. Cl.
  CPC .......... *A61B 17/0482* (2013.01); *A61B 17/34* (2013.01); *A61B 17/3403* (2013.01); *A61F 2/00* (2013.01); *A61M 5/158* (2013.01); *A61M 5/32* (2013.01); *A61M 37/00* (2013.01)

(58) Field of Classification Search
  CPC ........... A61F 2/00; A61M 5/158; A61M 5/32; A61M 37/00; A61M 5/329; A61M 2025/0081; A61M 25/0068; A61M 2025/1093
  See application file for complete search history.

(56) References Cited

FOREIGN PATENT DOCUMENTS

| | | | |
|---|---|---|---|
| KR | 101434976 B1 | 8/2014 | |
| KR | 101454659 B1 | 10/2014 | |
| KR | 1020140120720 A | 10/2014 | |
| KR | 101534814 B1 | 7/2015 | |
| KR | 1020150084641 A | 7/2015 | |
| KR | 1020150145578 | 12/2015 | |
| KR | 1020160039350 | 4/2016 | |
| KR | 2016057138 A | 5/2016 | |
| KR | 20160066831 A | 6/2016 | |
| KR | 20160074933 A | 6/2016 | |
| KR | 101635581 B1 | 7/2016 | |
| KR | 101665299 B1 | 10/2016 | |
| RU | 2011101283 A | 8/2012 | |
| WO | 2006023975 A2 | 3/2006 | |
| WO | WO-2010139479 A2 * | 12/2010 | .......... A61M 25/008 |
| WO | 2014013210 A1 | 1/2014 | |
| WO | 2014157913 A1 | 10/2014 | |

OTHER PUBLICATIONS

Korea Patent Office, "Notice of Allowance Regarding Korean Patent Application No. 10-2016-0082865", dated Dec. 29, 2017, p. 5, Published in: KR.
Korea Patent Office, "Office Action Regarding Korean Patent Application No. 10-2017-0069637", dated Nov. 28, 2018, p. 5, Published in: KR.
Korea Intellectual Property Office, "International Search Report for International Application No. PCT/KR2017/006930", dated Sep. 19, 2017, p. 5, Published in: KR.
Ark, Morris, "Examination Report No. 1 for Standard Patent Application No. 2017289017", dated Jun. 4, 2019, p. 6, Published in: AU.
Filippi, Markus, "Extended European Search Report Re Application No. 17820562.1", dated Nov. 15, 2019, p. 8, Published in: EU.
Japanese Patent Office, "Office Action Re Japanese Patent Application No. 2018-569101", dated Oct. 29, 2019, p. 7, Published in: JP.
Masalova, M.G., "Office Action Regarding Russian Patent Application No. 2019100487", dated Oct. 9, 2019, p. 13, Published in: RU.
Morris Ark, "Examination Report No. 2 for Standard Australian Patent Application No. 2017289017", dated Feb. 11, 2020, p. 6, Published in: AU.

* cited by examiner

LIFTING MEMBER

TECHNICAL FIELD

The present invention relates to a lifting member, which easily inserts a medical thread into a muscle and induces the generation of an autogenous material.

BACKGROUND ART

Autogenous materials are present in fibers constituting muscles of a human body. If a foreign substance invades the muscle, autogenous materials gather around the invaded foreign substance to protect the muscle against the invaded foreign substance. The autogenous materials are generated to protect the muscle, consequently strengthening the muscle.

There are numerous kinds of autogenous material. The autogenous material is a chemical factor that is released from artificially wounded tissue cells of some skin muscle tissues and brings about a series of physiological changes to the tissues to provide wound recovery conditions, which will be described below in more detail based on principles of electrobiology, piezoelectric science and general biological control theory. The chemical factor is converted into heat energy to dilate tiny blood vessels and to accelerate lymph circulation, which significantly increases the metabolic rate and enhances nutritional supplement for the wounded part, removes excrescent products through circulation of body fluids while promoting proteolysis of some tissues and increasing peripheral nerve transmitters, and reduce amounts of peptides and 5-hydroxylamine in serum by generating active materials in vascular nerves. Accordingly, information for neuronal regeneration or modulation of the wounded part is delivered to the central nervous system and combining specific biochemical materials present in the human body is expedited to provide effects of increasing human immune functions through facilitated circulation of body fluids, regulating organ functions in the human body and strengthening the muscle.

Technical Problems to be Solved

The present invention provides a lifting member which easily inserts a medical thread into a muscle and induces the generation of an autogenous material.

Technical Solutions

In accordance with an aspect of the present invention, there is provided a lifting member including a needle having a through hole which is formed therein along the longitudinal direction, and a medical thread coupled to the outer circumference of the needle, wherein the medical thread is finished to enwrap the end of the needle.

Here, the needle may include a deformable part formed by inwardly grinding the end of the needle.

The deformable part may include a pair of deformable parts, which are formed to be symmetrical with respect to the diameter direction of the needle.

The medical thread may further include an internal protrusion part positioned within the through hole of the needle.

The internal protrusion part may be exposed to a trailing edge of a hub coupled to the needle.

The lifting member may further include a cone-shaped cover formed on a leading edge of the medical thread.

The medical thread may include a body part positioned on the outer circumference of the needle, a bent part formed opposite to the body part, and a connection part formed between the body part and the bent part.

The connection part may be formed by thermal fusion.

The lifting member may further include a retraction part coupled to the leading edge of the medical thread and formed opposite to the medical thread along the longitudinal direction of the needle.

The medical thread may include a body part positioned on the outer circumference of the needle and a bent part formed opposite to the body part, and the retraction part is positioned within the bent part of the needle.

In accordance with another aspect of the present invention, there is provided a lifting member coupled to a needle having a through hole which is formed therein along the longitudinal direction, the lifting member including a lifting thread coupled to the outer circumference of the needle, wherein the lifting thread is coupled to the end of the needle and includes a plurality of base threads formed in the through hole of the needle.

Here, the needle may include a medical fluid hole formed along the longitudinal direction of the needle, the medical fluid hole being perpendicular to the through hole.

The medical fluid hole may include a plurality of medical fluid holes spaced apart from one another along the longitudinal direction.

In addition, the medical fluid hole may be formed in a region of the needle.

The end of the lifting thread may be coupled to the needle, the base threads may be coupled to the end to be elongated within the through hole of the needle, and a plurality of anchor parts may further be formed in the base threads.

The anchor parts may include a first anchor part forming an obtuse angle with respect to a direction in which the needle is coupled and a second anchor part forming an obtuse angle with respect to a direction in which the needle is retracted.

The lifting member may further include a porous mesh part coupled to an end of the lifting thread and formed along the outer circumference of the needle.

Here, the mesh part may be coupled to be fixed to the end of the lifting thread and may be separated from the needle when the needle is retracted.

The end of the lifting thread may be formed to have a leading edge having a hemispherical or conical shape in view of a direction in which the needle is inserted.

In addition, the end of the lifting thread may be coupled to the needle through a groove formed therein.

Advantageous Effects

As described above, in the lifting member according to the present invention, a deformable part is formed by grinding an end of a needle, thereby efficiently injecting a medical fluid.

In addition, in the lifting member according to the present invention, a mesh type medical thread is formed on the outer circumference of the needle, thereby easily manufacturing the lifting member and efficiently injecting the medical fluid.

In the lifting member according to the present invention, a lifting thread is formed on the outer circumference of the needle and a medical fluid hole is formed along the longitudinal direction of the needle, thereby easily injecting the medical fluid into the human body. In addition, since the lifting thread is configured to include an end connected to a leading edge of the needle and includes a mesh part formed on the outer circumference of the needle, a base thread formed in the needle and an anchor part coupled to the base thread, it can remain in the human body when the needle is retracted and has an increased contact section area in the human body, thereby easily generating an autogenous material.

BEST MODE FOR CARRYING OUT THE INVENTION

Hereinafter, preferred embodiments of the present invention will be described in detail with reference to the accompanying drawings such that those can easily be embodied by those skilled in the art.

Figure 1:
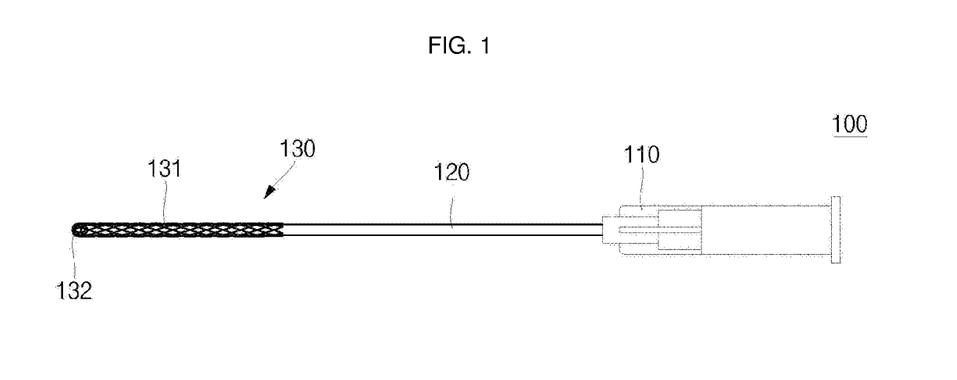
FIG. 1 is a cross-sectional view of a lifting member according to an embodiment of the present invention.
Figure 2A:
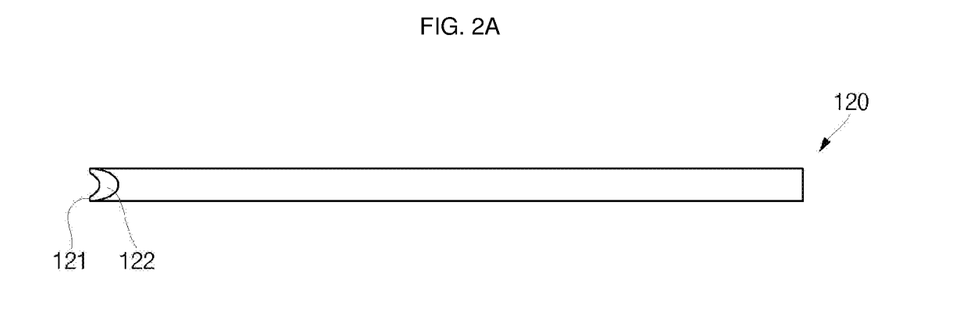
FIG. 2A is a plan view of a needle used in the lifting member according to an embodiment of the present invention.
Figure 2B:
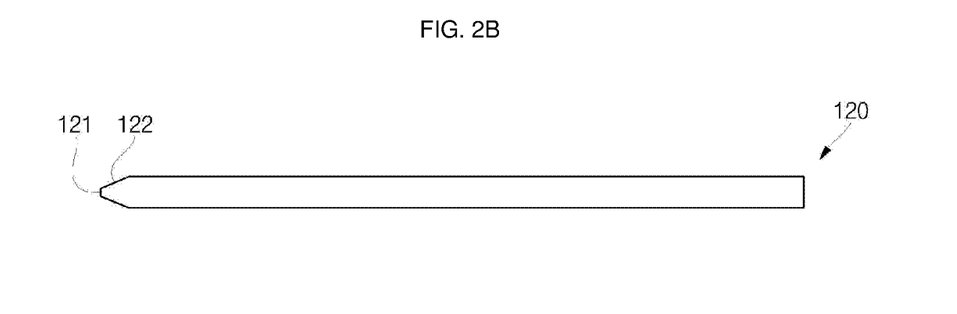
FIG. 2B is a side view of a needle used in the lifting member according to an embodiment of the present invention.
Figure 2C:
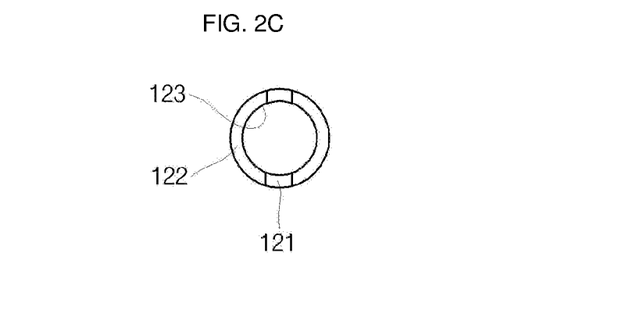
FIG. 2C is a front view of a needle used in the lifting member according to an embodiment of the present invention.

FIG. 1 is a cross-sectional view of a lifting member according to an embodiment of the present invention. FIG. 2A is a plan view of a needle used in the lifting member according to an embodiment of the present invention, FIG. 2B is a side view of a needle used in the lifting member according to an embodiment of the present invention, and FIG. 2C is a front view of a needle used in the lifting member according to an embodiment of the present invention.

First, referring to FIG. 1, the lifting member 100 according to an embodiment of the present invention may include a hub 110, a needle 120 and a medical thread 130.

The hub 110 may be coupled to a syringe, etc. at its trailing edge. The hub 110 may have a through hole formed therein to receive a medical fluid from the syringe and then transfer the received medical fluid to the needle 120.

The needle 120 is coupled to the hub 110 to then be exposed to a leading edge of the hub 110. The needle 120 may inject the received medical fluid into a human body through the medical thread 130.

Referring to FIGS. 2A to 2C, the needle 120 may include a deformable part 122 recessed from the end 121 to an interior portion. The deformable part 122 may include a pair of deformable parts formed to be longitudinally or laterally symmetrical with respect to the end 121 of the needle 120. The deformable part 122 may be formed by performing grinding from the end 121. That is to say, the deformable part 122 may be formed by longitudinally or laterally grinding the end 121 toward the interior portion.

Accordingly, the deformable part 122 may further open a through hole 123 formed in the needle 120 to opposite sides of the needle 120. Therefore, the medical fluid having passed through the through hole 123 may spread to sides of the needle 120 through the deformable part 122 and may more easily spread in the human body.

The medical thread 130 is coupled to the outer circumference of the outer circumference of the needle 120. That is to say, the medical thread 130 is formed to enwrap the needle 120 around the end 121 of the needle 120. In addition, the medical thread 130 may include a body part 131 formed along the needle 120 and an end 131 formed at an end of the body part 131 to correspond to the end 121 of the needle 120. Here, the end 131 prevents the end 121 of the needle 120 from protruding by finishing the body part 131. Therefore, when the medical thread 130 is inserted into the human body together with the needle 120, it is possible to prevent the needle 120 from being exposed to internal organ tissues of the human body.

In addition, the medical thread 130 may be made of a material that is degradable in the human body and may be in a form of a mesh as a whole. Therefore, when the medical thread 130 is inserted into the human body, the generation of an autogenous material can be promoted by increasing a contact area between the medical thread 130 and the human body. In addition, since a medical fluid injected from the needle 120 is delivered to the human body via interstices of the mesh, injection of the medical fluid can be efficiently performed.

In addition, since the medical thread 130 is formed along the outer circumference of the needle 120, it can be easily coupled to the needle 120 during the manufacture. In addition, the medical thread 130 is inserted into the human body together with the needle 120 to then easily remain even after the needle 120 is retracted for removal. Therefore, an operation using the medical thread 130 can be easily performed.

As described above, the lifting member 100 according to an embodiment of the present invention includes the deformable part 122 formed by grinding the end 121 of the needle 120, thereby efficiently injecting the medical fluid. In addition, since the lifting member 100 includes the mesh type medical thread 130 is formed along the outer circumference of the needle 120, the manufacture of the lifting member 100 can be facilitated and injection of the medical fluid can be efficiently performed.

Hereinafter, another type of a needle used in the lifting member according to an embodiment of the present invention will be described.

Figure 3A:
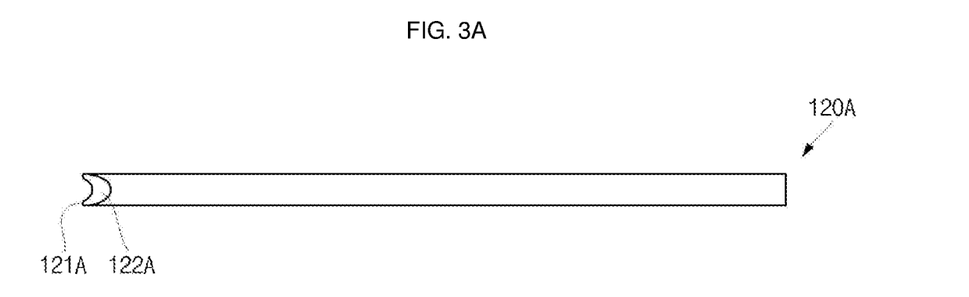
FIG. 3A is a plan view of another type of a needle used in the lifting member according to an embodiment of the present invention.
Figure 3B:
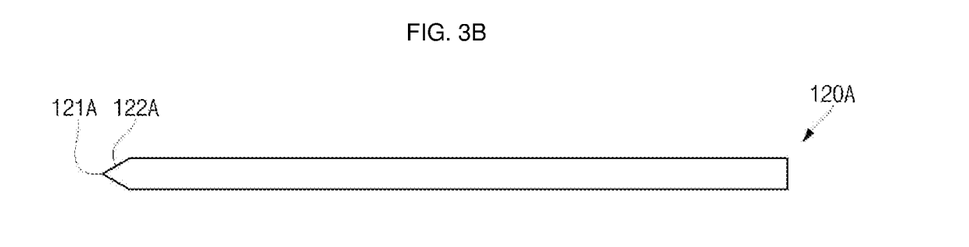
FIG. 3B is a side view of another type of a needle used in the lifting member according to an embodiment of the present invention.
Figure 3C:
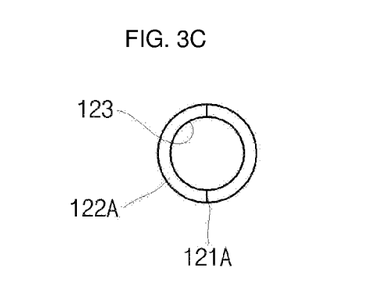
FIG. 3C is a front view of another type of a needle used in the lifting member according to an embodiment of the present invention.

FIG. 3A is a plan view of another type of a needle used in the lifting member according to an embodiment of the present invention, FIG. 3B is a side view of another type of a needle used in the lifting member according to an embodiment of the present invention and FIG. 3C is a front view of another type of a needle used in the lifting member according to an embodiment of the present invention.

Referring to FIGS. 3A to 3C, the needle 120A used in the lifting member 100 according to an embodiment of the present invention may include a deformable part 122A sharply grinded from an end 121A.

In the lifting member 100 according to an embodiment of the present invention, since a position of the medical thread 130 is stably fixed by the end 121A, the medical thread 130 can be inserted into a desired position.

Hereinafter, a configuration of another type of a needle used in the lifting member according to another embodiment of the present invention will be described.

Figure 4A:
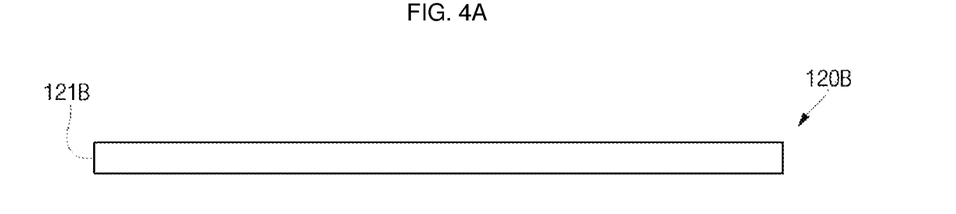
FIG. 4A is a plan view of still another type of a needle used in the lifting member according to an embodiment of the present invention.
Figure 4B:
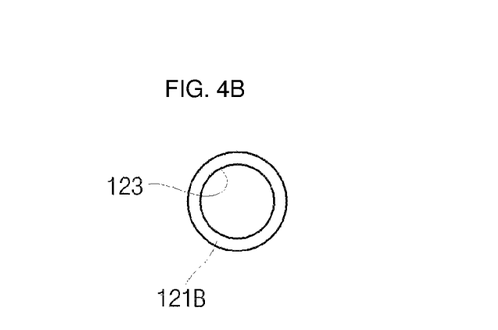
FIG. 4B is a front view of still another type of a needle used in the lifting member according to an embodiment of the present invention.

FIG. 4A is a plan view of still another type of a needle used in the lifting member according to an embodiment of the present invention and FIG. 4B is a front view of still another type of a needle used in the lifting member according to an embodiment of the present invention.

Referring to FIGS. 4A and 4B, the needle 120C used in the lifting member according to another embodiment of the present invention may have a planar end 121B. In the lifting member according to another embodiment of the present invention, it is possible to suppress human tissues from being damaged by the needle 120C when the needle 120C is inserted. In addition, since it is not necessary to separately process the needle 120C, the manufacturing process can be further simplified.

Hereinafter, a configuration of a lifting member according to another embodiment of the present invention will be described.

Figure 5:
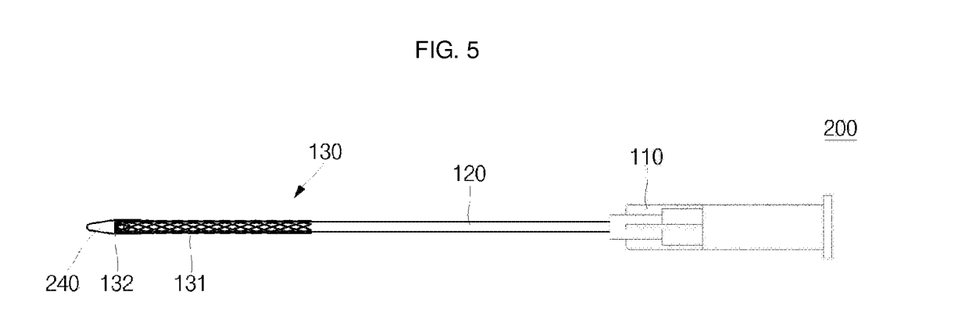
FIG. 5 is a cross-sectional view of a lifting member according to another embodiment of the present invention.

FIG. 5 is a cross-sectional view of a lifting member according to another embodiment of the present invention.

Referring to FIG. 5, the lifting member 200 according to another embodiment of the present invention may include a hub 110, a needle 120, a medical thread 130 and a cover 240. The elements having the same configurations and operations as those of the previous embodiment are denoted by the same reference numerals, and the following description will focus on differences between the current embodiment and the previous embodiment.

The cover 240 may be formed to correspond to a region where the end 121 of the needle 120 and the end 131 of the medical thread 130 are coupled to each other. Like the medical thread 130, the cover 240 may be made of a material that is degradable in the human body. In addition, the cover 240 is cone-shaped and functions as a guide for an insertion passageway when the needle 120 and the medical thread 130 are inserted into the human body. In addition, the cone-shaped cover 240 may prevent the human body from being damaged by the needle 120 when the needle 120 and the medical thread 130 are inserted into the human body.

Hereinafter, a configuration of a lifting member according to still another embodiment of the present invention will be described.

Figure 6:
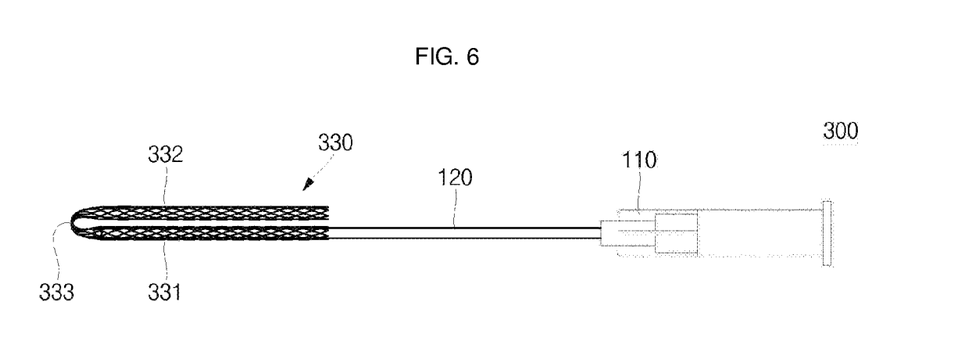
FIG. 6 is a cross-sectional view of a lifting member according to still another embodiment of the present invention.

FIG. 6 is a cross-sectional view of a lifting member according to still another embodiment of the present invention.

Referring to FIG. 6, the lifting member 300 according to still another embodiment of the present invention may include a hub 110, a needle 120 and a medical thread 330.

The medical thread 330 may include a body part 331 formed along the outer circumference of the needle 120, a bent part 332 bent opposite to the body part 331 and a connection part 333 connecting the body part 331 and the bent part 332.

Here, the bent part 332 may be formed to be symmetrical with respect to the body part 331. In addition, the connection part 333 may be formed in the middle of the body part 331 and the bent part 332. The connection part 333 may be formed by reducing the diameter of the bent part 332 by, for example, thermal compression. In this way, the connection part 333 can be formed in a finished structure, thereby allowing the medical thread 330 to be stably fixed on the outer circumference of the needle 120 without a separate element.

Hereinafter, a configuration of a lifting member according to still another embodiment of the present invention will be described.

Figure 7:
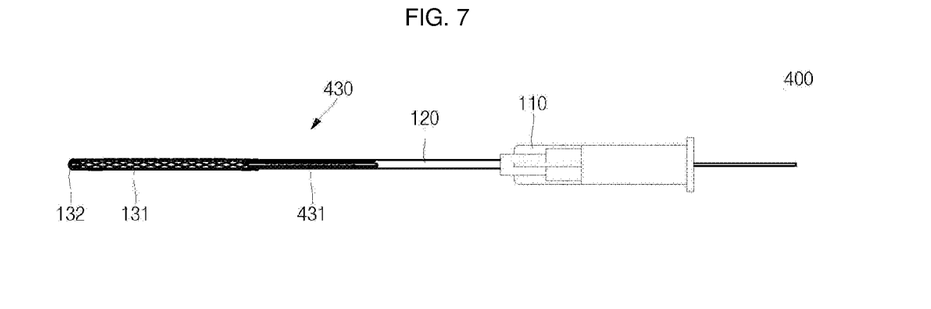
FIG. 7 is a cross-sectional view of a lifting member according to still another embodiment of the present invention.

FIG. 7 is a cross-sectional view of a lifting member according to still another embodiment of the present invention.

Referring to FIG. 7, the lifting member 400 according to still another embodiment of the present invention may include a hub 110, a needle 120 and a medical thread 430.

The medical thread 430 may include a body part 131, an end 132 and an internal protrusion part 431.

The internal protrusion part 431 is connected the body part 131 or the end 132 and is positioned within a through hole 123 of the needle 120. The internal protrusion part 431 remains in the human body when the needle 120 and the medical thread 130 are inserted into the human body and the needle 120 is then retracted for removal. In addition, the internal protrusion part 431 may increase a contact area in the human body through protrusions formed on its surface, thereby inducing the generation of an autogenous material.

In addition, the internal protrusion part 431 may be exposed to the trailing edge of the hub 110. Therefore, the body part 131 of the medical thread 430 may be varied to have a desired shape by an operator pulling the trailing edge of the hub 110 after the inserting of the medical thread 430 is completed.

Hereinafter, a configuration of a lifting member according to still another embodiment of the present invention will be described.

Figure 8:
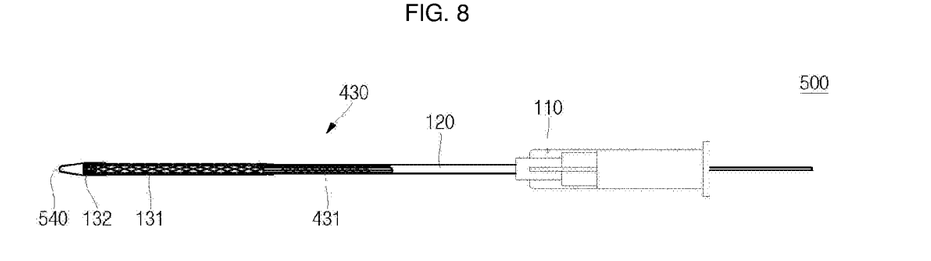
FIG. 8 is a cross-sectional view of a lifting member according to still another embodiment of the present invention.

FIG. 8 is a cross-sectional view of a lifting member according to still another embodiment of the present invention.

Referring to FIG. 8, the lifting member 500 according to still another embodiment of the present invention may include a hub 110, a needle 120, a medical thread 430, and a cover 540.

Here, the cover 540 has the same configuration and effect with the cover 240 of the lifting member 540 according to the previous embodiment. That is to say, the cover 540 may be made of a material that is degradable in the human body and may function as a guide when the needle 120 is inserted into the human body while protecting the human body.

Hereinafter, a configuration of a lifting member according to still another embodiment of the present invention will be described.

Figure 9:
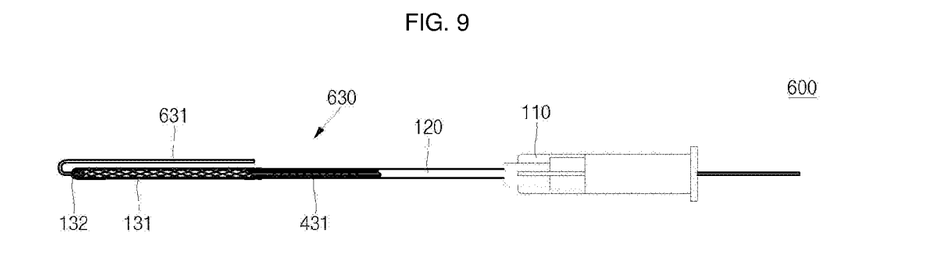
FIG. 9 is a cross-sectional view of a lifting member according to still another embodiment of the present invention.

FIG. 9 is a cross-sectional view of a lifting member according to still another embodiment of the present invention.

Referring to FIG. 9, the lifting member 600 according to still another embodiment of the present invention may include a hub 110, a needle 120, and a medical thread 630.

The medical thread 630 may include a body part 131, an end 132, an internal protrusion part 431, and a retraction part 631.

The retraction part 631 may be configured such that it is connected to the internal protrusion part 431. Alternatively, the retraction part 631 may extend in a direction in which it is retracted along the needle 120. The retraction part 631 may fix a position of the medical thread 130 in the human body. Therefore, in a case where an exposed end of the internal protrusion part 431 is pulled by an operator, the body part 131 may be varied to have a desired shape.

Hereinafter, a configuration of a lifting member according to still another embodiment of the present invention will be described.

Figure 10:
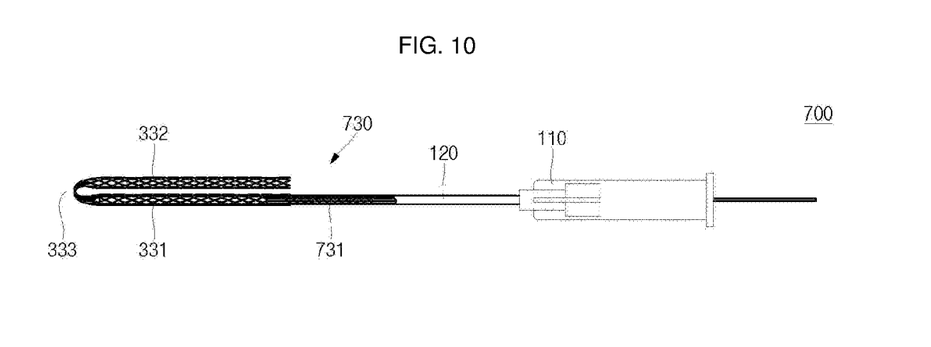
FIG. 10 is a cross-sectional view of a lifting member according to still another embodiment of the present invention.

FIG. 10 is a cross-sectional view of a lifting member according to still another embodiment of the present invention.

Referring to FIG. 10, the lifting member 700 according to still another embodiment of the present invention may include a hub 110, a needle 120, and a medical thread 730.

The medical thread 730 may include a body part 731, a bent part 332, a connection part 333, and an internal protrusion part 731.

Here, the internal protrusion part 731 is the same with the internal protrusion part 431 of the lifting member 400 according to the previous embodiment. Therefore, as described above, after being inserted into the human body, the internal protrusion part 731 may increase a contact area in the human body to facilitate the generation of an autogenous material, and the body part 331 may be varied to have a desired shape by an operator pulling a trailing edge of the internal protrusion part 731.

Hereinafter, a configuration of a lifting member according to still another embodiment of the present invention will be described.

Figure 11:
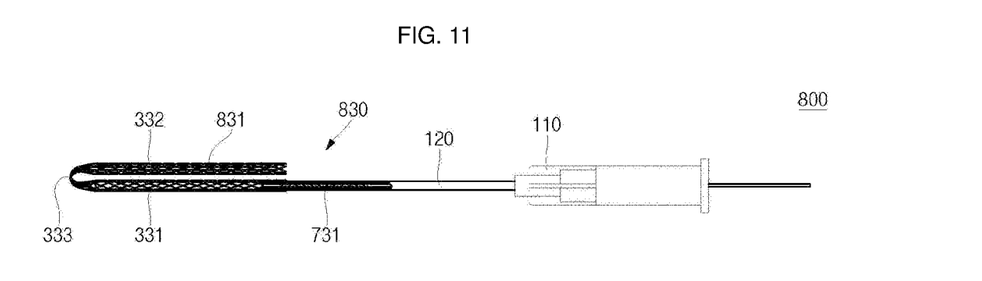
FIG. 11 is a cross-sectional view of a lifting member according to still another embodiment of the present invention.

FIG. 11 is a cross-sectional view of a lifting member according to still another embodiment of the present invention.

Referring to FIG. 11, the lifting member 800 according to still another embodiment of the present invention may include a hub 110, a needle 120 and a medical thread 830.

The medical thread 830 may include a body part 331, a bent part 332, a connection part 333, an internal protrusion part 731, and a retraction part 831.

The retraction part 831 may be positioned inside the bent part 332. The retraction part 831 may facilitate the generation of an autogenous material in the human body by increasing a contact area of the bent part 332. In addition, the bent part 332 is fixed by the retraction part 831, and the body part 331 may be varied to have a desired shape by externally pulling the internal protrusion part 731.

Hereinafter, a configuration of the lifting member according to still another embodiment of the present invention will be described.

Figure 12:
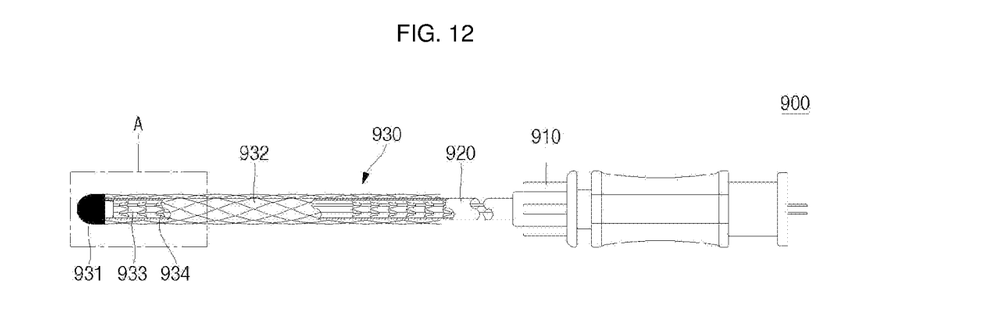
FIG. 12 is a cross-sectional view of a lifting member according to still another embodiment of the present invention.
Figure 13A:
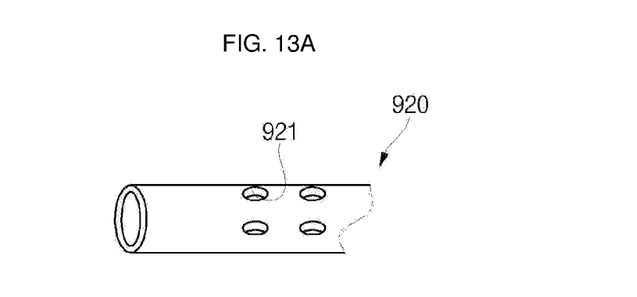
FIGS. 13A and 13B are cross-sectional views of needles used in a lifting member according to still another embodiment of the present invention.
Figure 13B:
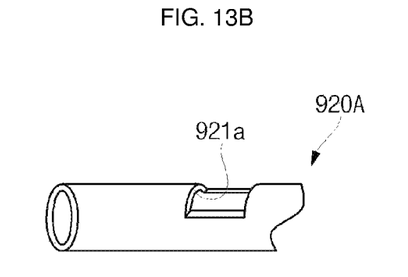
Figure 14:
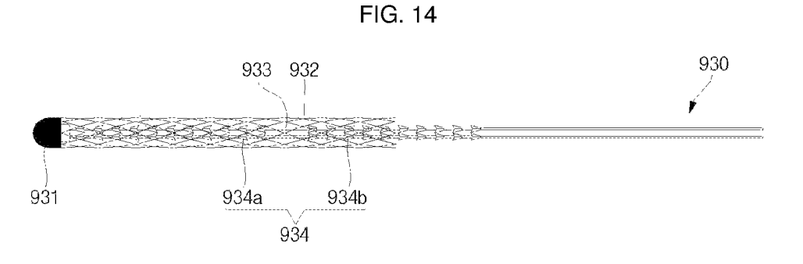
FIG. 14 is a cross-sectional view of a lifting thread used in a lifting member according to still another embodiment of the present invention.
Figure 15:
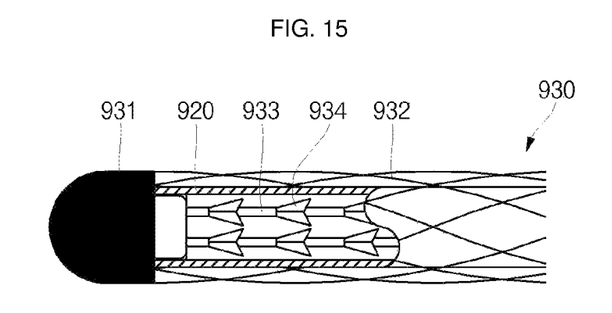
FIG. 15 is a partially enlarged view of a portion A of FIG. 12.

FIG. 12 is a cross-sectional view of a lifting member according to still another embodiment of the present invention. FIGS. 13A and 13B are cross-sectional views of needles used in the lifting member according to still another embodiment of the present invention. FIG. 14 is a cross-sectional view of a lifting thread used in the lifting member according to still another embodiment of the present invention. FIG. 15 is a partially enlarged view of a portion A of FIG. 12.

First, referring to FIG. 12, the lifting member 900 according to still another embodiment of the present invention may include a hub 910, a needle 920 and a lifting thread 930.

The hub 910 may be coupled to a syringe, etc. at its trailing edge. The hub 910 may have a through hole formed therein to receive a medical fluid from the syringe and then transfer the received medical fluid to the needle 920.

The needle 920 is coupled to the hub 910 to then be exposed to a leading edge of the hub 910. The needle 920 may inject the received medical fluid into a human body through the lifting thread 930.

Referring to FIG. 13A, the needle 920 may include a medical fluid hole 921 formed in at least one region of its circumference. The medical fluid hole 921 may include at least one medical fluid hole formed along the longitudinal direction of the needle 920. The medical fluid hole 921 allows the medical fluid moving along the longitudinal direction of the needle 920 to flow out. In particular, since the lifting thread 930 enwrapping the needle 920 is coupled to the end of the needle 920, the medical fluid injected through the needle 920 may require a passageway to be delivered to a human body. Therefore, the medical fluid hole 921 establishes a passageway for delivering the medical fluid in the human body.

Therefore, the medical fluid may pass through the medical fluid hole 921 and may then be delivered to and absorbed in the human body. Here, since the lifting thread 930 enwrapping the needle 920 is formed in a mesh type along the circumference of the needle 920, the medical fluid may pass through the lifting thread 930 as well to then be delivered to the human body. Accordingly, the lifting member 900 according to the current embodiment can deliver the medical fluid to the human body to then be easily absorbed in the human body, thereby further increasing a lifting effect.

Next, referring to FIG. 13B, a needle 920A may be configured to have a medical fluid hole 921a formed in a region of its circumference. In this case, the medical fluid hole 921a may be formed only at one region of the needle 920 and may be formed to have a relatively large area. In this case, since a medical fluid is delivered to a human body only in a direction in which the medical fluid hole 921a is formed, the medical fluid can be efficiently injected into a local body region.

The medical fluid hole 921, 921a may be formed by mechanically grinding or cutting the circumference of the needle 920, 920A. An operator may perform a grinding or cutting process on a predefined region of the circumference of the needle 920, 920A to form a hole extending through the thickness of the needle 920, 920A, thereby forming the medical fluid hole 921, 921a likewise.

The lifting thread 930 is coupled to the outer circumference of the needle 920. That is to say, the lifting thread 930 is formed to enwrap the circumference of the needle 920 about the end of the needle 920.

In addition, the lifting thread 930 may be made of a material that is degradable in the human body and the outer circumference may be formed in a mesh type. When the lifting thread 930 is inserted into the human body, the generation of an autogenous material can be promoted by increasing a contact area between the lifting thread 930 and the human body. In addition, since a medical fluid injected from the needle 920 is delivered to the human body via interstices of the mesh, injection of the medical fluid can be efficiently performed. In addition, the lifting thread 930 is inserted into the human body together with the needle 920 to then easily remain in the human body even after the needle 920 is retracted for removal. Therefore, an operation using the lifting thread 930 can be easily performed.

More specifically, to facilitate the operation of the lifting thread 930, the lifting thread 930 may include an end 931 coupled to the end of the needle 920, a mesh part 932 connected to the end and formed 931 along the outer circumference of the needle 920, a base thread 933 connected to the end 931 and elongated within the needle 920, and a plurality of anchor parts 934 spaced apart from one another along the longitudinal direction of the base thread 933.

The end 931 is coupled to the end of the needle 920 to prevent the end of the needle 920 from protruding. Therefore, when the lifting thread 930 is inserted into the human body together with the needle 920, it is possible to prevent internal organ tissues of the human body from being damaged by the needle 920. In addition, the end 931 may function to fix a position of the lifting thread 930 relative to the needle 920. In addition, in order to prevent internal organ tissues of the human body from being damaged by the end 931 when the lifting thread 930 is inserted, the end 931 may be formed to have a leading edge having a hemispherical or conical shape. Therefore, the end 931 can be inserted into the human body with reduced resistance without causing damages to the internal organ tissues of the human body.

In addition, since the end 931 is separated from the needle 920, the end 931, the mesh part 932 coupled to the end 931, the base thread 933 and the anchor parts 934 may remain in the human body even after the lifting thread 930 is inserted into the human body in a state in which it is coupled to the needle 920 and is then retracted for removal. In addition, since a trailing edge of the end 931 is substantially perpendicular to the end of the needle 920, the trailing edge of the end 931 may function as a kind of an anchor for the internal organ tissue when the needle 920 is retracted. Therefore, the end 931 can be easily inserted into the human body and can remain in the human body even after the needle 920 is retracted.

The mesh part 932 may extend in a longitudinal direction along the outer circumference of the needle 920 with its one end fixed by the end 931. The mesh part 932 is shaped of a mesh having holes formed therein. Therefore, the medical fluid flowing out through the medical fluid hole 921 of the needle 920 can be delivered to the human body via the mesh part 932. In addition, the mesh part 932 can increase a sectional area contacting internal organ tissues, thereby increasing the effect of generating an autogenous material around the mesh part 932.

The base thread 933 may be coupled to the end 931 to then be elongated within the needle 920 along the longitudinal direction of the needle 920. The base thread 933 may consist of a plurality of strands, and two strands of base threads are illustrated in the examples shown in FIGS. 14 and 15. Since the base thread 933 is coupled to the end 931, it can remain in the human body together with the end 931 when the needle 920 is retracted. In addition, since the base thread 933 includes a plurality of base threads, to which anchor parts 934 to be described later are coupled, respectively, a contact area between the plurality of base threads and internal organ tissues can be increased, thereby facilitating the generation of the autogenous material.

The anchor parts 934 include a plurality of anchor parts, which are spaced apart from one another along the longitudinal direction of the base threads 933. Specifically, the anchor parts 934 may include a first anchor part 934a forming an obtuse angle with respect to a direction in which the needle 920 is coupled and a second anchor part 934b forming an obtuse angle with respect to a direction in which the needle 920 is retracted. Each of the first anchor part 934a and the second anchor part 934b may include a plurality of first and second anchor parts, respectively. The anchor parts 934 may remain in the human body and may increase contact section areas, thereby facilitating the generation of an autogenous material in the human body.

As described above, the lifting member 900 according to still another embodiment of the present invention includes the lifting thread 930 formed on the outer circumference of the needle 920, while forming the medical fluid hole 921, 921a along the longitudinal direction of the needle 920, thereby allowing the medical fluid to be easily injected into the human body. In addition, the lifting thread 930 is configured to include the end 931 coupled to the leading edge of the needle 920, the mesh part 932 formed on the outer circumference of the needle 920 and coupled to the end 931, the base threads 933 formed within the needle 920 and the anchor parts 934 coupled to the base threads 933, thereby allowing the lifting thread 930 to remain in the human body when the needle 920 is retracted and easily generating the autogenous material by the increased contact section area in the human body.

Hereinafter, another type of a needle used in the lifting member according to still another embodiment of the present invention will be described.

Figure 16:
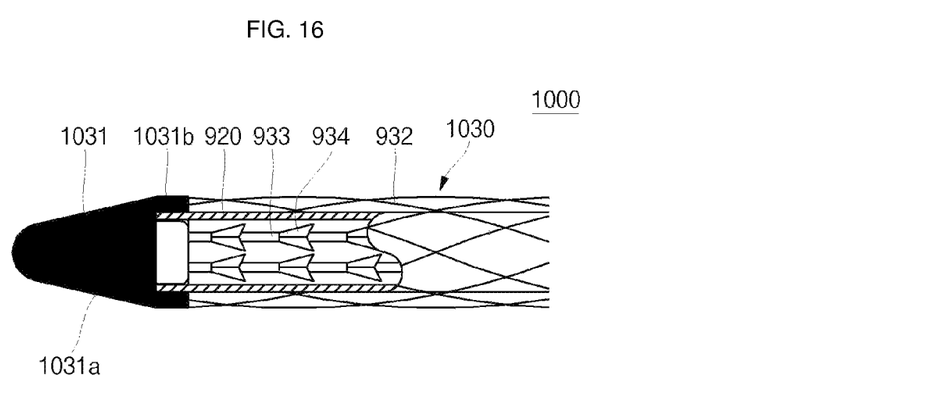
FIG. 16 is an enlarged view illustrating a cross section of a lifting member according to still another embodiment of the present invention.

FIG. 16 is an enlarged view illustrating a cross section of a lifting member according to still another embodiment of the present invention.

Referring to FIG. 16, the lifting member 100 according to still another embodiment of the present invention may include a hub (not shown), a needle 920 and a lifting thread 1030. The elements having the same configurations and operations as those of the previous embodiment are denoted by the same reference numerals, and the following description will focus on differences between the current embodiment and the previous embodiment.

The lifting thread 1030 is coupled to the outer circumference of the needle 920. That is to say, the lifting thread 1030 enwraps the needle 920 around an end of the needle 920.

In addition, the lifting thread 1030 may also be made of a material that is degradable in the human body and the outer circumference of the lifting thread 1030 may be in a form of a mesh.

More specifically, the lifting thread 1030 may include an end 1031 coupled to the end of the needle 920, a mesh part 932 coupled to the end 1031 of the lifting thread 1030 and formed along the outer circumference of the needle 920, a base thread 933 connected to the end 1031 and elongated within the needle 920, and a plurality of anchor parts 934 spaced apart from one another along the longitudinal direction of the base thread 933.

The end 1031 is coupled to the end of the needle 920 to prevent the end of the needle 920 from protruding. Specifically, the end 1031 may be configured to include a first region 1031*a* coupled to the needle 920 and exposed to a leading edge of the needle 920, and a second region 1031*b* coupled to the first region 1031*a* and actually coupled to the needle 920.

The first region 1031*a* may have a substantially conical shape having an inclined surface. In addition, the inclined surface may form an obtuse angle with respect to a direction in which the needle 920 is inserted into the human body. Therefore, the lifting thread 1030 is inserted into the human body through when the needle 920, the inserting of the lifting thread 1030 is performed along the inclined surface of the first region 1031*a*, thereby inserting the lifting thread 1030 into the human body with reduced resistance without causing damages to the internal organ tissues of the human body.

In addition, the second region 1031*b* is coupled to a trailing edge of the first region 1031*a* and is coupled to the needle 920 through an internal groove. Therefore, the second region 1031*b* may function to increase a bonding strength between the lifting thread 1030 and the needle 920. In addition, the second region 1031*b* may operate as an anchor against a retracting direction of the lifting thread 1030 when the needle 920 is retracted. Therefore, with the second region 1031*b*, the lifting thread 1030 can remain at a more accurate position in the human body. In addition, the second region 1031*b* may increase a contact section area in the human body, thereby facilitating the generation and bonding of an autogenous material.

Although the foregoing embodiments have been described to practice the lifting member of the present invention, these embodiments are set forth for illustrative purposes and do not serve to limit the invention. Those skilled in the art will readily appreciate that many modifications and variations can be made, without departing from the spirit and scope of the invention as defined in the appended claims.

INDUSTRIAL APPLICABILITY

The lifting member according to the present invention includes a deformable part formed by grinding an end of a needle, thereby efficiently injecting a medical fluid.

In addition, the lifting member according to the present invention includes a mesh type medical thread formed on the outer circumference of the needle, easily manufacturing the lifting member and efficiently injecting the medical fluid.

In addition, the lifting member according to the present invention includes a lifting thread formed on the outer circumference of the needle and a medical fluid hole formed along the longitudinal direction of the needle, thereby easily injecting the medical fluid into the human body. In addition, since the lifting thread is configured to include an end connected to the leading edge of the needle and includes a mesh part formed on the outer circumference of the needle, a base thread formed in the needle and an anchor part coupled to the base thread, it can remain in the human body when the needle is retracted and has an increased contact section area in the human body, thereby easily generating an autogenous material.

The invention claimed is:

1. A lifting member comprising:
   a needle having a through hole which is formed therein along a longitudinal direction; and
   a medical thread coupled to an outer circumference of the needle,
   wherein the medical thread is finished to enwrap an end of the needle, and wherein the needle includes a deformable part inwardly grinded from the end of the needle, wherein the deformable part includes a pair of deformable parts formed to be longitudinally or laterally symmetrical with respect to the end of the needle.

2. The lifting member of claim 1, wherein the medical thread further includes an internal protrusion part positioned within the through hole of the needle.

3. The lifting member of claim 2, wherein the internal protrusion part is exposed to a trailing edge of a hub coupled to the needle.

4. The lifting member of claim 1, further comprising a cone-shaped cover formed on a leading edge of the medical thread.

5. The lifting member of claim 1, wherein the medical thread includes a body part positioned on the outer circumference of the needle, a bent part formed opposite to the body part, and a connection part formed between the body part and the bent part.

6. The lifting member of claim 5, wherein the connection part is formed by thermal fusion.

7. The lifting member of claim 1, further comprising a retraction part coupled to a leading edge of the medical thread and formed opposite to the medical thread along the longitudinal direction of the needle.

8. The lifting member of claim 7, wherein the medical thread includes a body part positioned on the outer circumference of the needle and a bent part formed opposite to the body part, and the retraction part is positioned within the bent part.

9. A lifting member coupled to a needle having a through hole which is formed therein along a longitudinal direction, the lifting member comprising:
   a lifting thread coupled to an outer circumference of the needle,
   wherein the lifting thread is coupled to an end of the needle and includes a plurality of base threads formed in the through hole of the needle; and
   a porous mesh part coupled to an end of the lifting thread and formed along the outer circumference of the needle.

10. The lifting member of claim 9, wherein the needle includes a medical fluid hole formed along the longitudinal direction of the needle, the medical fluid hole being perpendicular to the through hole, and wherein the medical fluid hole is formed in a region of the needle.

11. The lifting member of claim 10, wherein the medical fluid hole includes a plurality of medical fluid holes spaced apart from one another along the longitudinal direction.

12. The lifting member of claim 9, wherein the end of the lifting thread is coupled to the needle, the base threads are coupled to the end of the needle to be elongated within the through hole of the needle, and a plurality of anchor parts are further formed in the base threads.

13. The lifting member of claim 12, wherein the anchor parts include a first anchor part forming an obtuse angle with respect to a direction in which the needle is coupled and a second anchor part forming an obtuse angle with respect to a direction in which the needle is retracted.

14. The lifting member of claim 9, wherein the mesh part is coupled to be fixed to the end of the lifting thread and is separated from the needle when the needle is retracted.

15. The lifting member of claim 9, wherein the end of the lifting thread is formed to have a leading edge having a hemispherical or conical shape in view of a direction in which the needle is inserted.

16. The lifting member of claim 9, wherein the end of the lifting thread is coupled to the needle through a groove formed therein.

* * * * *